United States Patent [19]

Gangadharan et al.

[11] Patent Number: 5,643,582
[45] Date of Patent: Jul. 1, 1997

[54] MOISTURIZER

[75] Inventors: Balgopal Gangadharan, Parsippany, N.J.; Marshall A. Hayward, Guildford, England; Denise Lynne Ward, Fairfield, N.J.

[73] Assignee: SmithKline Beecham Corporation, Philadelphia, Pa.

[21] Appl. No.: 307,679

[22] PCT Filed: Mar. 25, 1993

[86] PCT No.: PCT/US93/02975

§ 371 Date: Sep. 22, 1994

§ 102(e) Date: Sep. 22, 1994

[87] PCT Pub. No.: WO93/19733

PCT Pub. Date: Oct. 14, 1993

[51] Int. Cl.$^6$ .................................................. A61K 7/48
[52] U.S. Cl. ........................ 424/401; 424/427; 424/430; 424/434; 424/436; 514/938

[58] Field of Search ........................... 424/401, 427, 424/430, 434, 436; 514/938

[56] References Cited

U.S. PATENT DOCUMENTS

| | | | |
|---|---|---|---|
| 4,032,628 | 6/1977 | Papantoniou et al. | 424/63 |
| 4,300,820 | 11/1981 | Shah | 351/160 H |
| 4,347,237 | 8/1982 | Evenstad et al. | 424/78 |
| 5,004,598 | 4/1991 | Lochhead et al. | 424/59 |
| 5,066,709 | 11/1991 | Chaudhuri et al. | 524/516 |

FOREIGN PATENT DOCUMENTS

| | | |
|---|---|---|
| 0105657 | 4/1984 | European Pat. Off. . |
| 0431719 | 6/1991 | European Pat. Off. . |

*Primary Examiner*—Jyothsna Venkat
*Attorney, Agent, or Firm*—Nora Stein-Fernandez; William T. King; Edward T. Lentz

[57] ABSTRACT

This invention is a long acting moisturizer particularly suited for moisturizing the epithelia.

7 Claims, No Drawings

MOISTURIZER

FIELD OF THE INVENTION

This invention is a moisturizer for rehydrating or maintaining hydration in skin and mucous membranes using bioadhesives in combination with humectants and water complexing agents. In addition this moisturizer has lubricating properties derived from the moisturizing properties and unctuous components which make it useful in preventing abrasions or soreness and redness resulting from contact with other materials.

Moisturizers are widely available for treating topical skin problems like dry, flaking or cracked skin caused by loss of water, or abrasions and redness caused by exposure and rubbing. The consumer has many choices. But as a general rule skin lotions and skin conditioners fall into a limited group of types of formulations which can be broken out into two main categories, the oil-in-water emulsions and hydrophobic barriers illustrated by the likes of petrolatum. Many of these formulations can be used on either dermal or mucosal tissue and will work well on both types of tissue, at least on the short or very short term of a few hours or so.

Nearly all these products work by preventing or reducing moisture loss rather than adding moisture back to the skin. Petrolatum and similar products are among the best at preventing or reducing water loss, and since petrolatum adheres well to the skin, it's residence time and its affect is extended. The major draw-back to its use is that user acceptance is low because it is viewed as messy and unsightly; it does not absorb well into the skin and the skin has what is viewed a peculiar feel. Oil-in-water emulsions are usually more user acceptable as they are absorbed into the skin. but often they lack a sustainable affect; water evaporation from the formula, once applied to the skin is high, the barrier properties are relative low, and the formulation does not remain on the skin in a useful form for very long.

Attempts have been made to develop formulations which can replenish the water lost through normal evaporation. Some compounds such as glycerol and some amino acids like arginine have found some favor in these attempts and have been labeled humectants. Along with work on humectants, xerogels have been used in an attempt to increase the residence time on the skin of the water in the moisturizers. Some of these formulations may have lubricating properties as well, though this is not well documented. Two examples of interest in the context of one use of this invention is Lubrin sold by Upsher-Smith Labs Inc., a suppository for treating vaginal dryness and Replens marketed by Columbia Labs, Miami, Fla.

Unlike other moisturizers the one described here has both a short acting and a long acting component and the capability to adhere to and remain adhered to the site for up to several days. This is due to the use of two adhesive agents. One is immediately available when the moisturizer is applied. The other becomes available at a later time as the gust adhesive agent is being dissolved or eroded away. A composite particulate is used to provide both adhesives.

SUMMARY OF THE INVENTION

This invention has at least three aspects. One is a moisturizing cream per Se. A second embodiment is a method of producing this cream by combining two compositions at about the time of using the moisturizer. And the third is an article of manufacture where the two components are presented in separate vessels for combining in anticipation of immediate use.

More specifically, in a first aspect, this invention relates to a moisturizer for epithelial cells comprising a mixture of purified water, a water soluble polymer having bioadhesive properties, one or more preservatives, a humectant, a pharmaceutically acceptable oil, glycerides and bilayer polymeric particles comprising a hydrophobic adhesive polymer core coated with a water soluble, hydrophilic bioadhesive polymer.

In a second aspect, this invention relates to a moisturizing product, preferably a cream, for application to epithelial cells prepared by mixing two compositions from separate sources at about the time of applying the product wherein the first composition is an oil-in-water emulsion comprising purified water, a water soluble and swellable polymer having bioadhesive properties, a preservative, a humectant and a pharmaceutically acceptable oil, and the second is a dispersion of bilayer polymeric particles dispersed in a glyceride where the particles have a core of hydrophobic non-permanent adhesive surrounded by a layer of water soluble, hydrophilic bioadhesive material.

In a third aspect, this invention relates to an article of manufacture comprising a first and second vessel wherein one vessel contains an oil-in-water emulsion comprising purified water, a water soluble polymer having bioadhesive properties, a preservative, a humectant and a pharmaceutically acceptable oil, and the second is a dispersion of bilayer polymeric particles in a glyceride, the particles comprising a core of hydrophobic non-permanent adhesive surrounded by a layer of water soluble, hydrophilic bioadhesive material.

DETAILED DESCRIPTION OF THE INVENTION

One aspect of this invention is the moisturizer per Se. The formulation described below has the capacity to hydrate epithelial cells such as comprise the dermis and mucous membranes. It can be applied to any epithelial cell mass where hydration is to be maintained or where rehydration is needed. Examples of situations where this product may be useful is chapped and broken skin, particularly skin which has been exposed to sun, wind, salt water or cold weather, ocular tissue, the mucous membranes of the nasal passages, oral cavity, the vagina and the colon. When used as a vaginal moisturizing agent it can also act as a sexual lubricant. In addition to acting as a moisturizing agent, this formulation can serve as a delivery vehicle for therapeutic agents, serve as a pH modifying agent (or buffering agent), act as a vehicle for odor masking agents, contraceptive agents, or such other soluble or suspendable agents as one might wish to deliver to epithelial cell masses.

These compositions are substantially non-toxic to the animals in which or on which it is placed.

This moisturizer is unique in that it has the capacity to remain in place for an extended period, two to four days, all the while continuing to act as a moisturizing agent. These unique properties are achieved by employing the oil-in-water emulsion system in conjunction with selected water soluble, water swellable bioadhesives and certain glycerides each of which has inherent hydrating properties in their own right. In general terms, this mix of materials provides rehydration means immediately via an oil-in-water emulsion, selected humectants, and water absorbing glycerides with bioadhesives which immediately adheres to tissue and moisturize it. The bioadhesive is made available over an extended period by using bilayer particles where the outer coating of water-soluble polymer is quick acting; as it is sluffed off it exposes a second, less water soluble bioadhesive which provides a second-stage adhesive affect. Since the bioadhesive particles can be differentially coated to release core material at different times, an extended, constant supply of adhesive can be presented to the moisturizing system. One or more of the components, particularly the glycerine and glycerides, absorb water from the oil-in-water emulsion system and water given off from surrounding tissue, hold that water and release it back to the tissue over time, acting much like a reservoir. This reservoir is kept in place by the bioadhesives due to the fact they interact with the glycerides, forming a layer of water-containing material held in place via the adhesive properties of the bioadhesive polymer.

This moisturizer can be thought of as having two components, a first being the oil-in-water component and the second being the bilayer particulates dispersed in selected glycerides. The make-up of both components is illustrated in the following table.

TABLE I

| Component A | Component B |
| --- | --- |
| Purified water | Bilayer Particles |
| Preservative(s) | Glycerides |
| Water swellable bioadhesive | |
| Humectant | |
| Oil | |
| Glycerides | |

Component A can be used alone as a moisturizer if so desired.

Water makes up the largest fraction of Component A, an oil-in-water emulsion. Since this moisturizer is intended for human use, though it could be used on any animal, the water must be free of pathogens, toxins, chemicals which irritate the skin such as chlorine, dissolved or suspended solids, and any other deleterious or untoward materials. Water purification systems are well known and can be purchase from many manufacturers. Examples of such systems are reverse osmosis, activated carbon filters, deionizing systems, bacterial filters, and filtration devices to removed suspended solids. Distillation techniques may produce sufficiently pure water as well.

Preferably, between about 10% to 95% of Component A will be water. An amount between 50–90% is more preferable.

A water soluble, water swellable polymer with bioadhesive properties may be added to Component A to provide short-term bioadhesion in the period before the bioadhesive particle materials swell and become effective. In the context of Component A the basic property of such a bioadhesive is that it can form a non-permanent (breakable) bond between two epithelial surfaces.

A bioadhesive can be broadly defined as a material that adheres to a live or freshly killed biological surface such as mucous membrane or skin tissue. More specifically a "bioadhesive" may be define by several in vitro and ex vivo assays. One procedure for determining if a compound is a bioadhesive within the terms and usage of this invention is to determine the force required to move apart the two plates of a Chatillon gauge. In this assay, a 5% polymer suspension/dispersion is placed on the lower plate of the Chatillon gauge. The lower plate is brought up mechanically against the upper plate at a rate of 5.08 cm/min. A compression force of 50 kg is applied for 1 minute. Then the lower plate is pulled away at a rate of 5.08 cm/min. The amount of force applied to the separating plates at the moment of failure is taken as the measure of the tensile strength of the liquid polymer. Samples are tested within 24 hours of their preparation. Triplicate tests are done, preferably. "Bioadhesive" polymers are those with a tensile strength of between about 0.1–15.0 kg somewhere within the normal physiological pH range, eg. 1.5–8.0.

Another assay which can be used to identify a "bioadhesive" polymer within the scope of this invention is the one described in U.S. Pat. No. 4,615,697. That assay measures the force required to separate two layers of freshly excised rabbit stomach tissue that are adhered together by an adhesive. By the U.S. Pat. No. 4,615,697, a bioadhesive can be defined as a polymer that requires a force of at least about 50 dynes/cm$^2$ to separate the two adhered, freshly excised pieces of rabbit stomach tissue. More preferably, the force is at least about 380 dynes/cm$^2$. Upper limits for forces required to separate the freshly excised rabbit tissue are presently unknown, but are said to be at least about 2000 dynes/cm$^2$.

A number of polymers fit the two foregoing requirements. They are exemplified by the following list: gum guar, gum Arabic, Karaya gum, gelatine, gum tragacanth, gum acacia, pectin, celluloses (e.g. carboxymethyl cellulose derivatives), hydroxypropylmethyl cellulose (HMPC), polymethacrylates, acrylic acid polymers, cationic polyacrylamide, lower alkylvinyl ethers and their co-polymers (e.g. methylvinyl ether/maleic anhydride copolymers), polyalkylene oxides (e.g. ethylene oxide), polyvinyl pyrrolidones (PVP). This is not an exhaustive list but is meant to illustrate the nature of the polymer which can be used in this O/W component.

Such polymers will be present is amounts ranging between 0.1 and 15 percent by weight of Component A. A more preferred amount is 1.0 to 6.0 percent. Pure forms are to be used. Particle size is not a consideration as these are solubilized polymers in water.

All of the mentioned polymers are commercially available or can be extracted from natural sources by published methods. Gums, celluloses and other polymers from natural sources are available from a number of biological and chemical supply houses world-wide.

One or more humectants can be added to Component A. This is not an absolute requirement, but the moisturizers's performance in initial rehydration will be improved if one is used. In this context, the word humectant is intended to have the normal and regular meaning accorded it in the cosmetics arts. Examples are glycerin, polyethylene glycols, polypropylene glycols, urea, sodium pyroglutamate, 2-pyrrolidinone-5-carboxylic acid salts, amino acids, and the like. Glycerin is preferred. Humectants may be present in amounts ranging between 2.0 and 40.0 percent of Component A. A preferred amount is between 5.0 and 25.0 percent. These humectants are widely available from commercial sources.

Oil used in the Component A emulsion can be any cosmetically acceptable oil for a plant, animal or synthetic source. No special standards are required other than that the oil does not have an adverse affect on the skin or contain any deleterious materials or interact with the other components in the moisturizer to form a product which will have an unwanted affect. Vegetable oils, i.e., castor oil, cottonseed oil, corn oil, peanut oil, sesame oil, olive oil, and rapeseed oil can be used. Mineral oil or other synthetic oils can be used. Mineral oil is preferred. About 2.0 to 20.0 percent of the make up of Component A will comprise oil. A preferred amount is between 0.5 and 15 percent.

Certain 14 to 24 carbon glycerides may be included in Component A; they will also be present in Component B as a suspending agent for the bioadhesives. In Component A these glycerides serve at least three purposes. They are used as part of the "oil," for their capacity to attract water from the immediate environment and release it back over time, and as an emulsifier. These glycerides may also have occlusive characteristics. They can be a mono- di- or triglyceride where the acid has 14 to 24 carbons and is partially or fully saturated. Mixtures can be used as well. When they are used in Component A, they will comprise between about 0.10 and 10.0 percent of that formulation. Preferred glycerides are those sold by Eastman Kodak Co under the tradename Myverol. Myverol 18-99 in particular is useful in Component A.

One or more antimicrobial agent or antioxidant may be used to preserve and/or stabilize these formulations during manufacture and storage. Agents should be selected to address these two functions in both components of this emulsion, the aqueous and the oil components. This may necessitate using two agents in some instances. Any one or more of the large number of cosmetically and pharmaceutically acceptable preservatives may be used in Component A, or in a unified preparation for that matter. This list includes, for example, ethanol, ascorbyl palmitate, ethyl and methylparaben, butylated anisole, butylated hydroxytoluene, chlorobutanol, ethylenediamine, ethyl vanillin, monothioglycerol, phenethyl alcohol, phenylmercuric nitrate, propylparaben, sassafras oil, benzoic acid and its salts, sodium formaldehyde sulfoxylate, sodium metabisulfite, sorbic acid, sulfur dioxide, maleic acid, and propyl gallate. Preferred agents include parabens, particularly methyl paraben, sorbic acid, and benzoic acid and its salts. The latter can be used as an acidulant as well.

These moisturizers can act as carriers for medicaments and the like. Thus in addition to the moisturizing affect achieved when these compositions are applied, one can also provide a therapeutic entity. Locally acting agents or systemic agents may be delivered via these formulations. They may be used to deliver drugs for treating skin infections caused by microbes or parasites, abnormal skin proliferation diseases, anti-ageing phenomena, protective agents such as sun screens or barrier-creating materials. Ocular drugs can be included in formulations applied to the eye. Compositions intended to be inserted into a body cavity, such as the vagina, buccal cavity or anal cavity may Contain agents for treating local phenomena or may be used to deliver a drug intended to have a systemic affect. For example a vaginal moisturizer can contain an antimicrobial agent such as for treatment of bacterial and fungal infections, antiviral agents, and contraceptive preparations. A detailed review of vaginal therapeutic agents and antifertility agents can be found in the article by Bhattacharyya, A. K. & Zaneveld, L. J. D., *The Human Vagina*, editor E. S. E Havez & T. N. Evans, Elsevier/North-Holland Biomedical Press (1978). Similarly buccal and anal preparations antiinfective agents or may contain a systemically acting drug such as an analgesic, a peptide or the like.

For certain application of this invention, the pH of the composition is best lowered to accommodate Me local environment, such as when making a vaginal moisturizer. Secondly, these compositions can be used to effectively lower the local pH value. Common yeasts, fungi and other microbes that cause vaginal infections do not grow well at a pH value of 5 or below. As a consequence, the before-described moisturizing method also provides a method of inhibiting vaginal yeast and fungal infections by adjusting the pH value to between about 3–5. It may be necessary to add an acidulant to Component A if it does not have inherently the desired pH either as Component A or as the moisturizer per Se when combined with Component B. Any acidulant can be used so long as it is compatible with the other ingredients and does not impart a deleterious and untoward affect to the moisturizer.

Component A is manufactured by combining individual ingredients and forming a emulsion by standard techniques.

Component B is a bilayer polymeric bioadhesive particle dispersed in glycerides. The purpose of this component is to provide a bioadhesive which is active over an extended period and keeps the other moisturizing ingredients in contact with the treated area. It has been discovered that a particle comprising a hydrophobic polymer surrounded by a more water soluble bioadhesive polymer gives useful extended properties in the finished moisturizer.

Useful core-forming polymers are those hydrophobic polymer with non-permanent adhesive properties in a particulate form which is surrounded by a water-soluble coating of some son which may be an adhesive in and of itself when hydrated. Because polymer tackiness or release is moisture dependent, these particles will be essentially anhydrous in preparation and storage. Less than 5 percent water is believed to provide the most useful finished particles and when incorporated into a carrier or the like, a similar limitation is most useful.

For the purpose of this invention, "hydrophobic" is defined as a polymer which will not dissolve significantly in deionized water at room temperature after three days. Significantly here refers to a couple of percentage points. Hydrophilic means something which immediately dissolves in deionized water with agitation at room temperature.

Useful core material may be any hydrophobic polymer having adhesive properties sufficient to form a non-permanent (breakable) bond between two surfaces. Many naturally occurring gums and synthetic polymers may be used for this purpose. A non-comprehensive list includes: gum guar, gum Arabic, Karaya gum, gelatine, gum tragacanth, gum acacia, pectin, celluloses (e.g. carboxymethyl cellulose derivatives), hydroxypropylmethyl cellulose (HMPC), polymethacrylates, acrylic acid polymers, cationic polyacrylamide, lower alkylvinyl ethers and their co-polymers (e.g., methylvinyl ether/maleic anhydride copolymers), polyalkylene oxides (e.g., ethylene oxide), polyvinyl pyrrolidones (PVP), and the like.

All of these polymers are commercially available or can be extracted from natural sources by published methods. For example, lower alkylvinyl ether copolymers (maleic anhydride or maleic acid and the salts) and the PVPs can be purchased from International Speciality Polymers of Wayne, N.J., USA. Gantrez® and Plasdone® are the two trade names under which ISP sells these particular polymers. The Gantrez series, those useful as core adhesives, are denoted as S (MW ca 18,000 and 70,000) MS (MW ca 60,000–75,000) and AN (MW ca 18,000–80,000). Gums, celluloses and other polymers from natural sources are available from a number of biological and chemical supply houses worldwide.

The adhesive core can be spherical or irregular in shape or may be comprised of a number of particles. Single particles may be coated or if particles are small, they may be useful to aggregate several particles and coat them as a bundle. For example, fluidized bed coating technology may be used to coat individual particles where particle size is sufficiently large to be compatible with the coating apparatus. Alternatively, where particles are small, a granulation process may be the most useful means for coating the adhesive.

Polymer size (molecular weight) is not critical so long as the requisite adhesiveness (tackiness) is present.

In selecting a core polymer, it should be kept in mind that one or more polymers can be used, including polymers of different make-up. Furthermore, the core particulates may contain non-adhesive excipients which are bulking agent, or which have some inherent activity such as assisting with spreading the adhesive or enhancing its adhesive properties by physical or chemical means.

Preferred core polymers include the alkylvinyl ethers and their copolymers, particularly methylvinyl ether/maleic anhydride polymers (MVE/MA). A preferred polymer of this type is available under the name Gantrez AN 169; it is a methylvinyl ether/maleic anhydride copolymer with a molecular weight of about 67,000. Other useful Gantrez polymers are Gantrez S 97 and Gantrez MS 955. Another preferred group of adhesives are the polyvinyl pyrrolidones (PVP) of various molecular weight ranging from 12,000 to 2 million or thereabouts. These are available commercially or can be made by published methods. Commercial sources include the ISP of Wayne, N.J. which sells these PVPs under the name Plasdone. Further, there are cellulose gums produced by such companies as Aqualon Corp. of Wilmington, Del., USA. A preferred cellulose gum is Cellulose Gum 7H4XF and 7H3SXF sold by Aqualon.

The outer layer is a hydrophilic polymer. Any of the many water-soluble polymers currently available or which may be developed, including water-soluble forms of the hydrophobic adhesives recited above, can be used. Any naturally occurring or synthetic polymer may be used. Two preferred coating are the lower alkylvinyl ether/maleic acid copolymers, particularly the alkali metal salts of these copolymers, and polyvinyl pyrrolidones. The most preferred coatings are methylvinyl ether/maleic acid (or its Ca and Na salts) and a PVP material sold under the trade name Plasdone K 120 or K 90 by ISP.

Coatings can be comprised of a single polymer or mixtures of several different polymers. Choice is directed by any number of factors which include the desired release rate and the amount of moisture present in the environment where the product will be used. Methods for selecting a coating or coatings are given below. That information in combination with the general state of knowledge on polymer coatings of this type make it a simple task for one to optimize the coating selection.

Coatings will comprise between about 0.01 to 50% by weight of the core. Preferably the coating will comprise between 1 to 25% of the core.

A longer lasting adhesive product can be achieved via these coated particles by varying the coating thickness or varying the break-down characteristics of different populations in a finished product such as a denture cream adhesive. Both characteristics can be combined as a third means of increasing the life of the adhesive product. For example several batches of particulates can be prepared where the coating percentage varies stepwise, e.g. 0.1%, 1%, 2%, 5%, etc. Mixing particles from each of these batches gives a composition which provides a certain concentration of adhesive when the 0.1% coating is dissolved (or mechanically removed) and then at some later time more adhesive is released as the 1% coating is removed, and so on until the most heavily coated cores are exposed. By this means the holding power of the formulation can be replenished over a variable time. Alternatively the coating polymer makeup can be manipulated to effect a differential release rate. An example of this would be to combine water-soluble polymer X which has release rate Y with various concentrations of polymer A which has release rate B. This combination can then be applied at the same loading rate to core polymer, or can be applied in a series of different concentrations, i.e., of increasing thicknesses, to different batches of core particulates. Then by mixing coated particulates from several batches, formulations with extended release of adhesive can be made.

Core particle size is of secondary consideration to the invention itself, but will influence the ease of handling these formulations. By way of illustration, hyrophobic polymer is ground to an acceptable fineness, preferably between about sub-micron to about 250 microns and then coated with the water-soluble polymer by some means. Coating can be performed by any number of methods which are available for coating with water-soluble polymers. One procedure comprises dissolving the coating in a suitable-solvent, e.g. water, and spray it onto the fluidized core particles (Fluid-bed granulator) or wet granulate it with the core material (Planetary mixer). Or a single particle coating technique may be used. The coating solution is either sprayed on the fluidized core particle in a fluid-bed granulator or wet granulated with the core in a Planetary mixer to form either spheres or granules. Various levels of the coating may be applied to the same core by either means. These are illustrative methods and any method may be use so long as the technique provides the desired bilayer particulates.

When coating is completed, if a two part packaging approach will be used, moisture content is reduced to less than five percent by some means before dispersing it in the glyceride. It is expected that any drying method can be used so long as it reduce the moisture content below 5% and does not adversely affect the essential nature of the composition. Once dried, the particles should be handled in a manner which avoids exposing them to excess moisture unless it is planned to mix it with Component A immediately to provide a finished cream for final packaging.

Dried particles are then dispersed in a glyceride which can be the one used in Component A (if one was used) or one with similar chemical make-up and characteristics vis-a-vis water absorption. In this Component, these glycerides serve two seemingly divergent purposes. As a dispersant for the particles, these glycerides serve to exclude water and thus maintain intact the adhesive polymers. But when these glycerides are exposed to water, such as when mixed with Component A, they hydrate, taking up to 60% by their weight of water, then slowly release it back to the environment which they are contacting, all the while acting as an occlusive agent to prevent evaporation. These glycerol esters may be a in mono- di- or triesters where the acid(s) has 14 to 24 carbons and is partially or fully saturated. Mixed esters of glycerol and mixtures of mono- di- and triesters can be used as dispersing agents. When they are used in Component A, they will comprise between about 0.10 and 10.0 percent of that formulation; more preferably about 0.5 to 8.0. Eastman Kodak Co. of Tennessee, U.S.A. sells a line of mono-ester glycerides under the tradename Myverol. Any of these Myverol esters should be useful in these moisturizers. Myverol 18-99 or 18-50 are examples of two preferred monoesters.

Polymer particles will be present in these dispersions at concentrations ranging between about 0.1 to 25.0%, preferably between 0.5 and 20.0%. This is on a weight/weight basis and refers to the dispersion described as Component B above, not the finished moisturizer.

Dispersions comprising the polymer particles and the glyceride can be made by any convenient means known in the art. For example, a glyceride or glyceride mixture is melted and particles are added with stirring while simultaneously cooling the suspension.

Concentration figures stated above are with reference to concentrations in the separated Component; those ranges will be reduced proportionally when an aliquots from each is combined to make the cream. Accordingly for finished creams, meaning as it is applied to the skin, and derived from combining Component A and B in a 1:1 ratio, the following range concentrations are obtained: purified water—5 to 48%; preservative—0.035 to 0.35%; humectant—1.0 to 20.0%; water soluble polymer—0.05 to 7.5%; oil—0.25 to 10.0%; glycerides—3.0 to 80%; and bilayer polymer particles—0.05 and 12.5%. A preferred range is: purified water—25 to 45%, preservative—0.075 to 0.15%, water soluble polymer—0.5 to 3%, humectant—2.5 to 12.5%, oil 0.25 to 7.5%, glycerides—15 to 67%, and bilayer polymer particles—0.25 and 10.0%. While these figures are given with respect to a 1:1 ratio of A and B, the concentrations of components in A and B can be modified within the ranges given in Table I so as to permit a broader ratio of mixes, i.e. ratios ranging from 1:3 to 3:1.

In practice, a two vessel system is the preferred article of manufacture, one vessel contains component A and the other the second component B. At about the time of use, a portion of component A is mixed with a portion of component B and applied to site to be treated. A two component system serves the purpose of isolating the water soluble adhesive particles from the components making up the oil-in-water emulsion, thus delaying hydrating the adhesive particles until the product is actually used.

Packaging can take just about any form one desires given the ingredient list and what ever inherent limitations it may contain. Many moisturizers are packaged in multiple dispensing bottles. This can be done with this moisturizer but the gel-like characteristics it takes on may dictate using specially designed bottles and bottle openings to make dispensing easier. A preferred packaging is a two component system where the mix of ingredients listed as Component A are stored separately from those of Component B and discrete ratios of each are sampled and mixed at or about the time one wishes to apply the product.

If the formulator elects to combine all ingredients at once and package them as a finished product, it may be useful to provide the container with an enlarged mouth to assist with dispensing the resulting gel-like cream. A jar with a substantial opening might be used to accommodate access to the cream. Squeezable tubes such as toothpaste and hair gel tubes can be used. Alternatively, single-use tear-off packets can be provided so that the consumer can select a sealed packet which contains a single dose of the cream, tears off one end, and squeezes out the cream. A variation on this approach, particularly suited for vaginal use, could be a narrow tubular dispenser of about a 2 or 3 cm in diameter which is inserted into the vagina and the cream dispensed by means expelling the cream in situ, for example by means of a plunger.

Manufacturing this type of one-container product can be accomplished by preparing the two Components and then intimately mixing them prior to filling the containers.

In the preferred packaging format, a two vessel system, involves an attached or a detached configuration. In other words, two completely separate containers may be used in a regime where one dispenses a portion from each either at distinct times or simultaneously. A well-known example of this approach is the two bottle system provided in a box where the user squeezes out an aliquot from one bottle then takes the second bottle and dispenses a second aliquot onto the first, and mixes them together. This can be done on the skin or on a non-porous surface and then be applied to the skin or mucous membrane. If the aliquots are dispensed directly onto the dermis or mucous membrane mixing can be affected with the fingers or hand, for example, or a non-reactive device such as a wooden or plastic spatula. A spatula-like device may be incorporated into one of the bottle caps or provided as a separate enclosure.

In a variation on mixing with a two compartment systems, mixing can be effected by adding an output orifice which is straight or has mixing characteristics. By this means the components can be brought into intimate contact and be used as the cream emerges from the nozzle with out further mixing. For example since one of the uses is as a vaginal moisturizer, a device with an extended nozzle placed upstream from the two chambers containing A and B can be prepared in such a fashion as to provide mixing and delivery into the body cavity to about the approximate distance of intended use. Such a device could be prepared in single dose form or as a multi-dose container. The variations on this packaging form are numerous and are readily apparent to the experienced practitioner.

If a Component A/Component B packaging system is used, a discrete range of ratios of both components will need to be dispensed in order to optimize the resulting cream. Any ratio could be used, keeping in mind the limitations imposed by the ingredients in each Component. Because water from Component A is essential to the cream, Component A should make up at least 30% of the finished cream. At the other end of the range, Component B should represent at least 10% of the cream. Any ratio which falls within this range, or thereabouts will make a useful moisturizer. A simple one-to-one (1:1) ratio is easiest to remember and use; packaging is simplified as well.

Lubricating properties in certain applications such as when applied to the vaginal cavity are believed to be derived from the long term hydrating affects of this system, in addition to inherent lubricating properties derived from the fatty components and the bioadhesive polymers.

A composition of this invention can be administered by any number of means so long as it provides the desired contact between the epithelial cells and the composition. For example, the moisturizer can be applied by rubbing the composition over the area to be moisturized or it can be applied by hand, forceps, suppository, plunger, douche or other suitable instrument. Where the conjunctival epithelia are to be contacted, these composition (after mixing components A and B if provided that way) can be instilled into the precorneal pockets of the eyes. Where the buccal, nasal, anal and/or vaginal epithelia are to be contacted, the composition can be applied in the form of a suppository, by hand, forceps, or the like or by douche or the like or other suitable instrument or device.

The composition is left in place for a time sufficient for moisturization of the contacted area to occur. In all known circumstances, these moisturizers are eliminated from the body by a natural bodily mechanism, such as by dispersion or erosion caused mechanically or by an aqueous body fluid such as vaginal secretions, and by washing. The bioadhesive moisturizing polymer-containing composition can also be lost by mechanical action at the site of contact as by action of the eyelid on the eyeball or tongue in the buccal cavity. For mucosa, a bioadhesive moisturizing polymer adheres to the mucin that covers the membrane or to the membrane itself. Mucin is replaced within about 10 to about 20 hours, usually about every 17 hours, and the adhered bioadhesive moisturizing polymer can be lost with the mucin.

In so far as packaging materials are concerned, any number of off-the-shelf materials can be used, including plastics, metal containers, metal lined plastics and the like. If warranted, dispensing devices can be attached to the container for ease in dispensing the cream or one of the Components. Pump devices such as those used with skin creams and soap dispensers can be used. Syringes may be useful in certain applications. Squeeze tube technology can be used for preformed creams where it is not necessary to combine aliquots from distinct and separate sources to make the cream for contemporaneous use.

In terms of how much to apply, this will be governed in part by the selected location. If it is applied to the dermis, sufficient material will be dispensed and combined so as to cover the affected area and not result in an excessive residue. In other words, one will use this moisturizer on the skin just like one would use any other moisturizer. A similar approach can be taken to treating vaginal and anal mucosa. If applied to the eye, a small amount may be indicated to avoid a foreign body sensation in the eye.

Evaluation Methodology

One method for testing the water absorbing, retention and releasing properties of these moisturizers is as follows:

A known amount of formulation is placed in dialysis tubes and sealed. The sealed tubes (in triplicate) are submerged in a distilled water bath maintained at room temperature. The percent weight gain of each bag, determined by weighing the bag and its accessories, is recorded over a period of about 24 hours or more. After the test period, the tubes are removed from the bath and the loss of water over 24 or 48 hours recorded by weighing the closed tubes.

A set of examples to illustrate the formulations and practice of this invention are given below. These Examples are just that, examples, and are not intended to limit the scope of the claimed invention, nor is it intended that they should they be so interpreted. Reference is made to the claims for what is reserved to the inventors.

EXAMPLE 1

Component A Formulation Preparation

An oil-in-water emulsion was prepared for mixing with the bilayer polymer dispersions recited in later Examples. An emulsion was prepared using the following ingredients.

| Ingredients | Amount (W/W %) |
|---|---|
| Purified water | 79.64 |
| Methyl paraben | 0.18 |
| Sorbic acid | 0.08 |
| CMC Na 7H4XF | 3.00 |
| Glycerin | 11.90 |
| Myverol 18-99 | 1.00 |
| Mineral oil | 4.20 |

CMC is carboxymethylcellulose. Here it is used in the sodium salt form as provided by Aqualon Co. Myverol is the trade name for a distilled monoglyceride sold by Eastman Kodak. An emulsion was formed using standard techniques.

EXAMPLE 2

Component B—Formulation Preparation

A coated particle employing an alkylvinyl/maleic anhydride polymer was prepared using the ingredients given in Table IA and IB.

TABLE IA

Coated Adhesive Particles

| Ingredients | Amount (% W/W) |
|---|---|
| Adhesive Core Material | |
| Methylvinyl ether/maleic anhydride (Gantrez AN 169, MW 67,000) | 72.72% |
| Polyvinyl pyrrolidone (PVP K 30, MW 42,000) | 18.18 |
| Coating Material | |
| Methylvinyl ether/maleic acid Ca/Na mixed salts (Gantrez MS 955) | 9.10 |
| | 100.00% |

Guar gum, Karaya gum, PVPs and other adhesive polymers may be substituted for the methylvinyl ether/maleic anhydride or PVP K 30 in the above composition. Combinations of two or more of these polymers, including the MVE/MA-PVP mix will also act as a useful core adhesive.

TABLE IB

| Ingredients | Amount (% W/W) |
|---|---|
| Adhesive Core Material | |
| Guar gum | 90.90 |
| Methylvinyl ether/maleic acid Ca/Na mixed salts (Gantrez MS 955) | 9.10 |
| | 100.00% |

Coated particle were prepared as follows: In a planetary mixer was dry blended Gantrez AN 169 and Plasdone K 30 for fifteen minutes. A previously prepared Gantrez MS 955 binder solution (10% Gantrez MS 955 in water) was then added into the planetary mixer over a period of about 20 minutes. Blending was continued until a uniformly moist granular mass was obtained. This mass was screened through a #14 mesh (1400 microns) sieve and transferred to drying trays for drying at about 45 degrees C. for 6 to 8 hours. Trays were removed from the dryer, cooled and the dried product passed through a #60 (250 microns) mesh screen and tested for moisture content to assure it was less that 5%. Dried material was stored in a bulk for later use.

A dispersion of these dried particles was prepared using a mixture of Myverol 18-99 (71.43%) and Myverol 18-50 (23.81%) and 4.76 grams of particles. This was accomplished by melting the two Myverols together, adding the particles with stirring to form a dispersion.

EXAMPLE 3

Moisturizing Cream

Equal portions of the oil-in-water emulsion prepared in Example 1 and the dispersion prepared in Example 2 were dispensed and mixed by hand to form a smooth cream which can be applied to the skin.

What is claimed is:

1. A moisturizer for the epithelia comprising a first component consisting essentially of a mixture of purified water (5 to 48%), a water soluble water swellable polymer having bioadhesive properties (0.05 to 7.5%), one or more preservatives (0.035 to 0.35%), a humectant (1.0 to 20.0%), and a pharmaceutically acceptable oil (1.0 to 10.0%), and a second component consisting essentially of a 14 to 24 carbon atom mono-, di-, or tri-glyceride and bilayer particles comprising bioadhesive polymers wherein the core is a lower alkylvinyl ether/maleic anhydride coated with an alkylvinyl ether/maleic acid salt.

2. The moisturizer of claim 1 where the water soluble polymer of the first component is a cellulose derivative selected from the group consisting of carboxymethyl cellulose, carboxymethyl cellulose sodium salt and hydroxypropylmethyl cellulose, the oil is a vegetable or mineral oil and the glyceride is a monoglyceride.

3. The moisturizer of claim 2 wherein the first component consists essentially of a mixture of purified water, a preservative, carboxymethyl cellulose, glycerin, mineral oil, and a monoglyceride.

4. The moisturizer of claim 2 wherein the first component consists essentially of a mixture of purified water in an amount between about 25 to 45%, a preservative in an amount between about 0.075 to 0.15%, carboxymethyl cellulose sodium salt in an amount between about 0.5 to 3%, humectant which is glycerin in an amount between about 2.5 to 12.5%, a pharmaceutically acceptable oil which is mineral oil in an amount between about 0.25 to 7.5%, the monoglyceride in an amount between about 15 to 67%; and bilayer polymer particles in an amount between about 0.25 and 10.0%.

5. A method for moisturizing vaginal tissue comprising applying a moisturizer according to claim 1 to the tissue.

6. A moisturizer for the epithelia comprising a first component consisting essentially of a mixture of purified water (5 to 48%), a preservative (0.035 to 0.35%) carboxymethyl cellulose (0.05 to 7.5%), glycerin (1.0 to 20.0%) and mineral oil (1.0 to 10.0%), and a second component consisting essentially of a monoglyceride (3.0 to 80.0%) and bilayer particles comprising bioadhesive polymers wherein the core is a lower alkylvinyl ether/maleic anhydride coated with an alkylvinyl ether/maleic acid salt.

7. The moisturizer of claim 6 which comprises purified water in an a mount between about 25 to 45%, the preservative in an amount between 0.075 to 0.15%, carboxymethyl cellulose in an a mount between about 0.5 to 3%, glycerin in an amount between about 2.5 to 12.5%, mineral oil in an amount between 0.25 to 7.5%, the monoglyceride in an amount between 15 to 67%, and bilayer polymer particles in an amount between 0.25 to 10.0%.

* * * * *